United States Patent [19]
Neumann et al.

[11] Patent Number: 5,976,498
[45] Date of Patent: Nov. 2, 1999

[54] METHODS OF DIAGNOSTIC IMAGE ANALYSIS USING METAL COMPLEXES OF NITROGEN-CONTAINING MACROCYCLIC LIGANDS

[76] Inventors: William L. Neumann, 844 Reindeer Dr., Ballwin, Mo. 63021; Dennis P. Riley, 800 Chancellor Hts. Dr., Ballwin, Mo. 63011; Randy H. Weiss, 3074 Woodbridge Estates, St. Louis, Mo. 63129; Susan L. Henke, 123 Parsons Ave., Webster Groves, Mo. 63119; Patrick J. Lennon, 7540 Wydown Blvd., Clayton, Mo. 63105; Karl W. Aston, 1940 Sunflower Ridge, Pacific, Mo. 63069

[21] Appl. No.: 08/698,612

[22] Filed: Aug. 16, 1996

Related U.S. Application Data

[60] Provisional application No. 60/002,422, Aug. 17, 1995.

[51] Int. Cl.$^6$ ............................. A61K 49/00; G01N 31/00
[52] U.S. Cl. ...................... 424/9.1; 424/9.362; 424/9.3; 424/9.4; 424/9.5; 424/1.65; 514/184; 514/186; 514/161
[58] Field of Search ............... 424/9.361, 9.362, 424/1.11, 9.1, 9.3, 9.36, 9.4, 9.42, 9.5, 9.6, 9.7, 9.8; 514/184, 186, 161; 548/100; 540/1, 474, 450, 465; 534/15, 16

[56] References Cited

U.S. PATENT DOCUMENTS

| | | | |
|---|---|---|---|
| 4,001,212 | 1/1977 | Richman | 260/239 |
| 5,049,667 | 9/1991 | Schaefer et al. | 540/474 |
| 5,064,956 | 11/1991 | Kruper, Jr. | 540/474 |
| 5,162,109 | 11/1992 | Rajagopalan et al. | 424/1.1 |
| 5,292,868 | 3/1994 | Subramanian | 530/391.5 |
| 5,322,681 | 6/1994 | Klaveness | 424/9 |
| 5,417,960 | 5/1995 | Schaefer et al. | 424/9.363 |
| 5,556,968 | 9/1996 | Carvalho et al. | 540/460 |
| 5,610,293 | 3/1997 | Riley et al. | 540/474 |
| 5,637,578 | 6/1997 | Riley et al. | 514/186 |
| 5,721,361 | 2/1998 | Lennon et al. | 540/450 |
| 5,874,421 | 2/1999 | Riley et al. | 514/161 |

FOREIGN PATENT DOCUMENTS

| | | |
|---|---|---|
| 9639396 | 12/1996 | WIPO. |
| WO 96/39396 | 12/1996 | WIPO. |

*Primary Examiner*—José G. Dees
*Assistant Examiner*—Dameron Jones
*Attorney, Agent, or Firm*—Monsanto Company

[57] ABSTRACT

The present invention is directed to complexes represented by the formula:

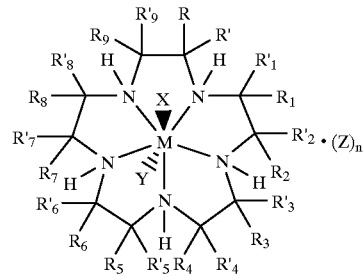

wherein R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, M, X, Y, Z and n are defined herein for use as contrast agents in diagnostic imaging.

17 Claims, No Drawings

METHODS OF DIAGNOSTIC IMAGE ANALYSIS USING METAL COMPLEXES OF NITROGEN-CONTAINING MACROCYCLIC LIGANDS

This application claims the benefit of U.S. Provisional Application No. 60/002,422, filed Aug. 17, 1995.

BACKGROUND OF THE INVENTION

This invention relates to compounds effective as contrast agents in diagnostic imaging. In one aspect, this invention relates to magnetic resonance imaging (MRI) of human or non-human animal subjects using metal complexes of substituted nitrogen-containing fifteen-membered macrocyclic ligands as contrast agents. In another aspect, this invention relates to manganese(II) complexes of substituted nitrogen-containing fifteen-membered macrocyclic ligands as MRI contrast agents.

X-rays have long been used to-produce images of human and non-human animal tissue, e.g. the internal organs of a patient, the patient being positioned between a source of X-rays and a film sensitive to the rays. Where organs interfere with the passage of the rays, the film is less exposed and the resulting developed film is indicative of the state of the organ.

More recently, nuclear magnetic resonance (NMR) has been developed as an imaging technique, i.e. MRI. MRI avoids the harmful effects sometimes attending X-ray exposure. For improved imaging with X-rays, patients have been given enhancers prior to imaging, either orally or parenterally. After a predetermined time interval for distribution of the enhancer through the patient, the image is taken. To obtain a good image it is desirable that the time after the taking of enhancer be kept to a minimum. On the other hand there is a decrease in effectiveness with time, so desirably the decay should be relatively slow so as to provide a substantial time interval during which imaging can be done.

In the NMR imaging process, protons in the water of the body relax via two mechanisms. The respective relaxation times are referred to as $T_1$ and $T_2$. The rate at which the relaxation process occurs may be altered for some water molecules by giving values that contrast with the norm.

Compounds that enhance NMR images, referred to as contrast agents, are generally paramagnetic in nature. These may be organic free radicals or transition/lanthanide metals which have from one to seven unpaired electrons.

A necessary prerequisite of any ligand that binds a metal to form a contrast agent is that the resulting contrast agent be stable so as to prevent the loss of the metal and its subsequent accumulation in the body. Other considerations include an ability to reversibly bind water, which in turn increases it contrastability and decreases the dose level required. This ability is clearly important since the interaction between any two nuclear spins through space decreases at a rate equal to the reciprocal of the distance raised to the sixth power.

U.S. Pat. No. 4,647,447 discloses use of an NMR image enhancer consisting of the salt of an anion of a complexing acid and a paramagnetic metal anion. A preferred embodiment is the gadolinium chelate of diethylenetriaminepentaacetic acid (Gd DTPA), which is now commercially available from Nycomed Salutar, Inc. under the trade name Magnevist for use as an NMR contrast agent. From the data reported therein these appear to perform well. However, this compound is rapidly excreted by the kidneys, making the timing of the injection extremely critical. Furthermore, there is virtually no uptake by any solid organ, such as the heart, pancreas or liver.

However, while a number-of gadolinium contrast agents are known, there remains the possibility that small amounts of free lanthanides are being released, by decomposition of the agent, into the body. Not being a naturally existing metal in the body, little is known about long term effects.

Other nitrogen-containing macrocyclic ligands have been suggested for use as NMR contrast agents. Jackels, S. C. et al, "Aqueous Proton NMR Relaxation Enhancements by Manganese(II) Macrocyclic Complexes: Structure-Relaxivity Relationships", *Inorg. Chem.*, 31, 234–239 (1992) discloses fifteen-membered nitrogen-containing ring complexes. However, these compounds suffer from being insufficiently stable and/or colored, and as such are inadequate for application as MRI contrast agents.

Therefore, it would be highly desirable to develop alternative contrast agents which avoid one or more of the aforementioned disadvantages.

It has now been discovered that metal complexes of substituted nitrogen-containing macrocyclic ligands which have increased kinetic, thermodynamic and oxidative stability, and which can be substituted to control lipophilicity, i.e. biodistribution, avoid the problems of the aforementioned contrast agents while providing good contrastability.

SUMMARY OF THE INVENTION

It is an object of the invention to provide magnetic resonance imaging (MRI) contrast agents having kinetic stability, i.e. the rate at which the paramagnetic metal dissociates from the metal complexes of the invention. It is a further object of the invention to provide MRI contrast agents in which the biodistribution of the contrast agents can be controlled. It is yet a further object of the invention to provide MRI contrast agents having oxidative stability and hydrogen bonding. It is a still further object of the invention to provide metal complexes which are useful as X-ray or ultrasound contrast agents, and which can be used in scintigraphy and radiotherapy.

According to the invention, a method of magnetic resonance imaging is provided which comprises administering to a human or non-human animal subject a contrast medium comprising a physiologically compatible paramagnetic metal complex of the present invention and a non-toxic, pharmaceutically acceptable carrier, adjuvant or vehicle, and generating a magnetic resonance image of at least a part of the subject.

Further according to the invention, a method of diagnostic imaging is provided which comprises administering to a human or non-human animal subject a diagnostic agent comprising a physiologically compatible heavy metal complex of the present invention and a non- toxic, pharmaceutically acceptable carrier, adjuvant or vehicle, and generating an X-ray, ultrasound or scintigraphic image of at least a part of the subject.

Further according to the invention, a method of radiotherapy practiced on a human or non-human animal subject is provided which comprises administering to the subject a radioactive agent comprising a physiologically compatible radioactive metal complex of the present invention and a non-toxic, pharmaceutically acceptable carrier, adjuvant or vehicle.

DETAILED DESCRIPTION OF THE INVENTION

The metal complexes of the invention used as MRI contrast agents, as diagnostic agents in X-ray, ultra-sound or scintigraphic image analysis, or as radiotherapy agents are represented by the formula:

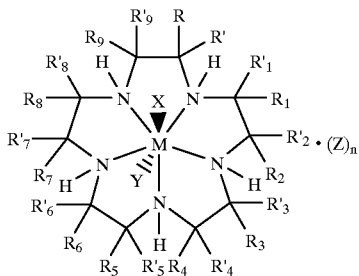

wherein at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$, and $R_7$ or $R'_7$ and $R_8$ or $R'_8$ are substituted alkyl, substituted alkenyl, substituted alkynyl, substituted cycloalkyl or substituted cycloalkenyl radicals wherein the substituents are independently selected from the group consisting of $-OR_{10}$, $-NR_{10}R_{11}$, $-COR_{10}$, $-CO_2R_{10}$, $-CONR_{10}R_{11}$, $-O-(-(CH_2)_a-O)_b-R_{10}$, $-SR_{10}$, $-SOR_{10}$, $-SO_2R_{10}$, $-SO_2NR_{10}R_{11}$, $-N(OR_{10})(R_{11})$, $-P(O)(OR_{10})(OR_{11})$, $-P(O)(OR_{10})(R_{11})$ and $-OP(O)(OR_{10})(OR_{11})$; or at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$ and $R_7$ or $R'_7$ and $R_8$ or $R'_8$ are independently selected wherein one "R" group of the pair is an alkyl, alkenyl, alkynyl, cycloalkyl or cycloalkenyl radical and the other "R" group on the adjacent carbon atom of the macrocycle is a substituted alkyl, substituted alkenyl, substituted alkynyl, substituted cycloalkyl or substituted cycloalkenyl radical wherein the substituents are independently elected from the group consisting of $-OR_{10}$, $-NR_{10}R_{11}$, $-COR_{10}$, $-CO_2R_{10}$, $-CONR_{10}R_{11}$, $-O-(-(CH_2)_a-O)_b-R_{10}$, $-SR_{10}$, $-SOR_{10}$, $-SO_2R_{10}$, $-SO_2NR_{10}R_{11}$, $-N(O_{10})(R_{11})$, $-P(O)(OR_{10})(OR_{11})$, $-P(O)(OR_{10})(R_{11})$ and $-OP(O)(OR_{10})(OR_{11})$; or combinations thereof; wherein $R_{10}$ and $R_{11}$ are independently selected from the group consisting of hydrogen and alkyl groups, and a and b are integers independently selected from 1 to 6; and the remaining "R" groups are hydrogen or, optionally, are independently selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$l $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not maintain a hydrogen attached to the nitrogen, the hydrogen attached to the nitrogen in said formula, which nitrogen is also in the macrocycle and the R groups attached to the same carbon atoms of the macrocycle are absent; and combinations thereof.

The currently preferred optional "R" groups are alkyl radicals, radicals attached to the α-carbon of α-amino acids, and saturated, partially saturated or unsaturated cyclic ring structures having 3 to 20 carbon atoms. Currently, $R_{10}$ and $R_{11}$ are preferably hydrogen.

X, Y and Z represent suitable ligands or charge-neutralizing anions which are derived from any monodentate or polydentate coordinating ligand or ligand system or the corresponding anion thereof (for example benzoic acid or benzoate anion, phenol or phenoxide anion, alcohol or alkoxide anion). X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid (such as acetic acid, trifluoroacetic acid, oxalic acid), aryl carboxylic acid (such as benzoic acid, phthalic acid), urea, alkyl urea, aryl urea, alkyl aryl urea, thiourea, alkyl thiourea, aryl thiourea, alkyl aryl triourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphsphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate aryl thiocarbamate, alkyl aryl thiocarbamate, alkyl dithiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or systems where one or more of X,Y and Z are independently attached to one or more of the "R" groups, wherein n is an integer from 0 to 3. The preferred ligands from which X, Y and Z are selected include halide, organic acid, nitrate and bicarbonate anions.

The metal atoms or anions, M, which are suitable for use in the complexes of the invention as MRI contrast agents are paramagnetic metals having atomic numbers 21–29, 42–44 and 57–71. The complexes for use as MRI contrast agents are those wherein the preferred metal is Eu, Gd, Dy, Ho, Cr, Mn or Fe, more preferably Gd(III) or Mn(II), and most preferably Mn(II).

The metal atoms or anions, M, which are suitable for use in the complexes of the invention as X-ray or ultrasound contrast agents are heavy metals having atomic numbers 20–32, 42–44, 49 and 57–83. The complexes for use as X-ray or ultrasound contrast agents are those wherein the preferred metal is a non-radioactive metal having atomic numbers 42–44, 49 and 57–83, and most preferably Gd, Dy or Yb.

The metal atoms or anions, M, of the complexes of the invention which are suitable for use in scintigraphic and radiotherapy are radioactive metals of any conventional complexable radioactive metal isotope, preferably those having atomic numbers 20–32, 42–44, 49 and 57–83. In scintigraphy, the most preferred metals are $^{99m}$Tc or $^{111}$In. In radiotherapy, the most preferred metals are $^{153}$Sm, $^{67}$Cu or 90Y.

Currently, the preferred compounds are those wherein at least one pair of "R" groups on adjacent carbon atoms of the macrocycle selected from the group consisting of $R_9$ or $R'_9$ and R or R', $R_1$ or $R'_1$ and $R_2$ or $R40_2$, $R_3$ or $R'_3$ and $R_4$ or $R'_4$, $R_5$ or $R'_5$ and $R_6$ or $R'_6$, and $R_7$ or $R'_7$ and $R_8$ or $R'_8$ are substituted alkyl, substituted alkenyl, substituted alkynyl, substituted cycloalkyl or substituted cycloalkenyl radicals wherein the substituents are independently selected from the group consisting of —$OR_{10}$, —$NR_{10}R_{11}$, —$COR_{10}$, —$CO_2R_{10}$, —$CONR_{10}R_{11}$, —O—(—$(CH_2)_a$—O)$_b$—$R_{10}$, —$SR_{10}$, —$SOR_{10}$, —$SO_2R_{10}$, —$SO_2NR_{10}R_{11}$, —$N(OR_{10})(R_{11})$, —$P(O)(OR_{10})(OR_{11})$, —$P(O)(OR_{10})(R_{11})$ and —$OP(O)(OR_{10})(OR_{11})$, more preferably —$OR_{10}$ or —$NR_{10}R_{11}$, and most preferably —$OR_{10}$; and the remaining "R" groups are hydrogen or, optionally, are independently selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$, and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent; and combinations thereof. Even more preferred are compounds wherein the "R" groups of the at least one pair of "R" groups on adjacent carbon atoms of the macrocycle are substituted alkyl groups, and the substituents are preferably —$OR_{10}$ and more preferably —OH.

Another preferred group of compounds are those wherein at least one pair of "R" groups on adjacent carbon atoms of the macrocycle selected from the group consisting of $R_9$ or $R'_9$ and R or R'$R_1$ or $R'_1$ and $R_2$ or $R'_2$, $R_3$ or $R'_3$ and $R_4$ or $R'_4$, $R_5$ or $R'_5$ and $R_6$ or $R'_6$ and $R_7$ or $R'_7$ and $R_8$ or $R'_8$ are independently selected wherein one "R" group of the pair is an alkyl, alkenyl, alkynyl, cycloalkyl or cycloalkenyl radical and the other "R" group on the adjacent carbon atom of the macrocycle is a substituted alkyl, substituted alkenyl, substituted alkynyl, substituted cycloalkyl or substituted cycloalkenyl radical wherein the substituents are independently selected from the group consisting of —$OR_{10}$, —$NR_{10}R_{11}$, —$COR_{10}$, —$CO_2R_{10}$, —$CONR_{10}R_{11}$, —O—(—$(CH_2)_a$—O)$_b R_{10}$, —$SR_{10}$, —$SOR_{10}$, —$SO_2R_{10}$, —$SO_2NR_{10}R_{11}$, —$N(OR_{10})(R_{11})$, —$P(O)(OR_{10})(OR_{10})$, —$P(O)(OR_{10})(R_{11})$ and —$OP(O)(OR_{10})(OR_{11})$, more preferably —$OR_{10}$ or —$NR_{10}R_{11}$, and most preferably —$OR_{10}$; and the remaining "R" groups are hydrogen or, optionally, are independently selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent; and combinations thereof. Even more preferred are compounds wherein one "R" group of the at least one pair of "R" groups on adjacent carbon atoms of the macrocycle is an alkyl group and the other "R" group on the adjacent carbon atom of the macrocycle is a substituted alkyl group, and the substituent on the carbon atom of the at least one pair of "R" groups on adjacent carbon atoms of the macrocycle which is a substituted group is —$OR_{10}$, and more preferably —OH.

As used herein, "R" groups means all of the R groups attached to the carbon atoms of the macrocycle, i.e., R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$ and $R'_9$. Examples of complexes of the invention include, but are not limited to, compounds having the formulas:

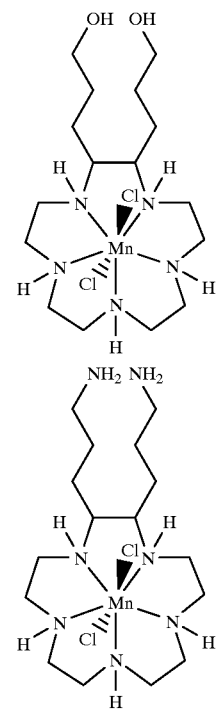

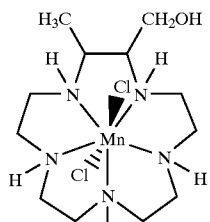

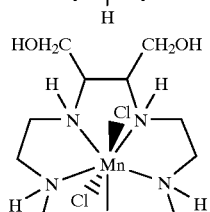

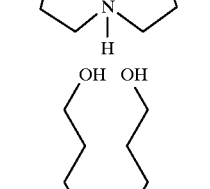

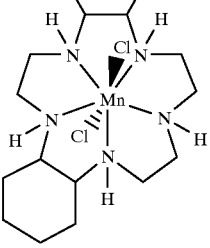

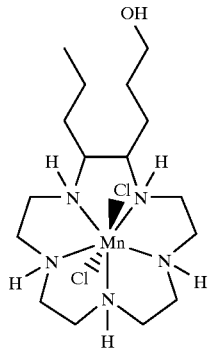

As utilized herein, the term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms which optionally carries one or more substituents selected from (1) —$NR_{30}R_{31}$ wherein $R_{30}$ and $R_{31}$ are independently selected from hydrogen, alkyl, aryl or aralkyl; or $R_{30}$ is hydrogen, alkyl, aryl or aralkyl and $R_{31}$ is selected from the group consisting of —$NR_{32}R_{33}$, —OH, —$OR_{34}$,

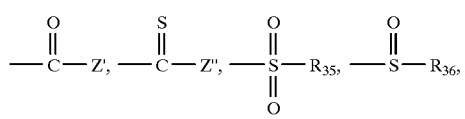

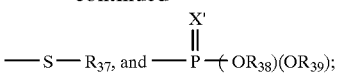

wherein $R_{32}$ and $R_{33}$ are independently hydrogen, alkyl, aryl or acyl, $R_{34}$ is alkyl, aryl or alkaryl, Z' is hydrogen, alkyl, aryl, alkaryl, —$OR_{34}$, —$SR_{34}$ or —$N_{40}R_{41}$ wherein $R_{40}$ and $R_{41}$ are independently selected from hydrogen, alkyl, aryl or alkaryl, Z" is alkyl, aryl, alkaryl, —$OR_{34}$, —$SR_{34}$ or —$NR_{40}R_{41}$, $R_{35}$ is alkyl, aryl, —$OR_{34}$, or —$NR_{40}R_{41}$, $R_{36}$ is alkyl, aryl or —$NR_{40}R_{41}$, $R_{37}$ is alkyl, aryl or alkaryl, X' is oxygen or sulfur, and $R_{38}$ and $R_{39}$ are independently selected from hydrogen, alkyl or aryl;

(2) —$SR_{42}$ wherein $R_{42}$ is hydrogen, alkyl, aryl, alkaryl, —$SR_{34}$, —$NR_{32}R_{33}$,

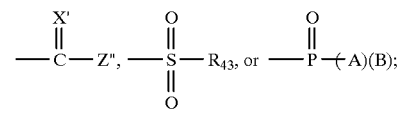

wherein $R_{43}$ is —OH, —$OR_{34}$ or —$NR_{32}R_{33}$, and A and B are independently —$OR_{34}$, —$SR_{34}$ or —$NR_{32}R_{33}$;

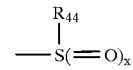

(3)

wherein x is 1 or 2, and $R_{44}$ is alkyl, aryl, alkaryl, —OH, —$OR_{34}$, —$SR_{34}$ or —$NR_{32}R_{33}$;

(4) —$OR_{45}$ wherein $R_{45}$ is hydrogen, alkyl, aryl, alkaryl, —$NR_{32}R_{33}$,

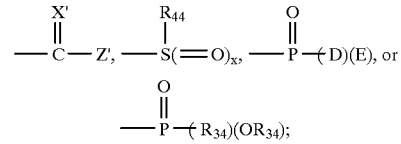

wherein D and E are independently —$OR_{34}$ or —$NR_{32}R_{33}$;

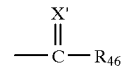

(5)

wherein $R_{46}$ is —OH, —SH, —$OR_{34}$, —$SR_{34}$ or —$NR_{32}R_{33}$; or (6) amine oxides of the formula

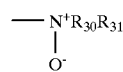

provided $R_{30}$ and $R_{31}$ are not hydrogen; or

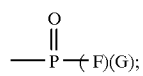

(7)

wherein F and G are independently —OH, —SH, —OR$_{34}$, —SR$_{34}$ or —NR$_{32}$R$_{33}$; or (8) halogen, cyano, nitro, or azido. Alkyl, aryl and alkaryl groups on the substituents of the above-defined alkyl groups may contain one additional substituent but are preferably unsubstituted. Examples of such radicals include, but are not limited to, methyl, ethyl, n-propyl, isopropyl, n-butyl, isobutyl, sec-butyl, tert-butyl, pentyl, isoamyl, hexyl, octyl, nonyl, decyl, dodecyl, tetradecyl, hexadecyl, octadecyl and eicosyl. The term "alkenyl", alone or in combination, means an alkyl radical having one or more double bonds. Examples of such alkenyl radicals include, but are not limited to, ethenyl, propenyl, 1-butenyl, cis-2-butenyl, trans-butenyl, iso-butylenyl, cis-2-pentenyl, trans-2-pentenyl, 3-methyl-l-butenyl, 2,3-dimethyl-2-butenyl, 1-pentenyl, 1-hexenyl, 1-octenyl, decenyl, dodecenyl, tetradecenyl, hexadecenyl, cis- and trans-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl. The term "alkynyl", alone or in combination, means an alkyl radical having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl. The term "cycloalkyl", alone or in combination means α--ycloalkyl radical containing from 3 to about 10, preferably from 3 to about 8, and most preferably from 3 to about 6, carbon atoms. Examples of such cycloalkyl radicals include, but are not limited to, cyclopropyl, cyclobutyl, cyclopentyl, cyclohexyl, cycloheptyl, cyclooctyl, and per-hydronaphthyl. The term "cycloalkylalkyl" means an alkyl radical as defined above which is substituted by a cycloalkyl radical as defined above. Examples of cycloalkylalkyl radicals include, but are not limited to, cyclohexylmethyl, cyclopentylmethyl, (4-isopropylcyclohexyl)methyl, (4-t-butyl-cyclohexyl methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl)methylheptyl. The term "cycloalkylcycloalkyl" means a cycloalkyl radical as defined above which is substituted by another cycloalkyl radical as defined above. Examples of cycloalkylcycloalkyl radicals include, but are not limited to, cyclohexylcyclopentyl and cyclohexylcyclohexyl. The term "cycloalkenyl", alone or in combination, means a cycloalkyl radical having one or more double bonds. Examples of cycloalkenyl radicals include, but are not limited to, cyclopentenyl, cyclohexenyl, cyclooctenyl, cyclopentadienyl, cyclohexadienyl and cycloqctadienyl. The term "cycloalkenylalkyl" means an alkyl radical as defined above which is substituted by a cycloalkenyl radical as defined above. Examples of cycloalkenylalkyl radicals include, but are not limited to, 2-cyclohexen-1-ylmethyl, 1-cyclopenten-1-ylmethyl, 2-(l-cyclohexen-1-yl)ethyl, 3-(l-cyclopenten-l-yl)propyl, 1-(1-cyclohexen-1-ylmethyl)pentyl, 1-(1-cyclopenten-1-yl)hexyl, 6-(1-cyclohexen-1-yl)hexyl, 1-(1-cyclopenten-1-yl)nonyl and 1-(1-cyclohexen-1-yl)nonyl. The terms "alkylcycloalkyl" and "alkenylcycloalkyl" mean a cycloalkyl radical as defined above which is substituted by an alkyl or alkenyl radical as defined above. Examples of alkylcycloalkyl and alkenylcycloalkyl radicals include, but are not limited to, 2-ethylcyclobutyl, 1-methylcyclopentenyl, 1-hexylcyclopentyl, 1-methylcyclohexyl, 1-(9-octadecenyl)cyclopentyl and 1-(9-octadecenyl)cyclohexyl. The terms "alkylcycloalkenyl" and "alkenylcycloalkenyl" means a cycloalkenyl radical as defined above which is substituted by an alkyl or alkenyl radical as defined above. Examples of alkylcycloalkenyl and alkenylcycloalkenyl radicals include, but are not limited to, 1-methyl-2-cyclopentenyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl. The term "aryl", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy) phenyl, 4-fluorophenyl, 4-chlorophenyl, 4-hydroxyphenyl, 1-naphthyl, 2-naphthyl, and the like. The term "aralkyl", alone or in combination, means an alkyl or cycloalkyl radical as defined above in which one hydrogen atom is replaced by an aryl radical as defined above, such as benzyl, 2-phenylethyl, and the like. The term "heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. The term "saturated, partially saturated or unsaturated cyclic" means fused ring structures in which 2 carbons of the ring are also part of the fifteen-membered macrocyclic ligand. The ring structure can contain 3 to 20 carbon atoms, preferably 5 to 10 carbon atoms, and can also contain one or more other kinds of atoms in addition to carbon. The most common of the other kinds of atoms include nitrogen, oxygen and sulfur. The ring structure can also contain more than one ring. The term "saturated, partially saturated or unsaturated ring structure" means a ring structure in which one carbon of the ring is also part of the fifteen-membered macrocyclic ligand. The ring structure can contain 3 to 20, preferably 5 to 10, carbon atoms and can also contain nitrogen, oxygen and/or sulfur atoms. The term "nitrogen containing heterocycle" means ring structures in which 2 carbons and a nitrogen of the ring are also part of the fifteen-membered macrocyclic ligand. The ring structure can contain 2 to 20, preferably 4 to 10, carbon atoms, can be partially or fully unsaturated or saturated and can also contain nitrogen, oxygen and/or sulfur atoms in the portion of the ring which is not also part of the fifteen-membered macrocyclic ligand. The term "organic acid anion" refers to carboxylic acid anions having from about 1 to about 18 carbon atoms. The term "halide" means chloride or bromide.

The overall charge-type-of the complex can be varied from negative to positive by carbon substitution of the appropriate charged groups on the macrocyclic framework. While the manganese (II) complexes of the invention exist as monocations in methanol solution, the axial anions are labile and in vivo can rapidly exchange with endogenous charged or uncharged ligands. By considering the dipositive nature of the manganese (II) metal center, the overall charge on the complex can be adjusted as needed to enhance desired pharmaceutical properties such as osmolality, tissue distribution and non-target clearance. For example, if the complex carries only charge neutral functionality, such as C-alkyl substitution, then the overall charge on the complex will be determined by the manganese center and will be positive. Multi-positive complexes are available via the incorporation of pendant cations such as protonated aminoalkyl groups. These types of complexes can bind to endogenous anions, anionic proteins, cell membranes, and the like. If two pendant anionic groups are attached, such as two carboxylates, phenolate, phosphonates, sulfonates and the like, the overall charge on the complex can be envisioned as zero. Alternatively, if three or more pendant anionic groups are attached, then an anionic complex will result. The pendant groups may be designed to axially chelate and formally displace the axial anions or they may be designed specifically to not chelate but retain a charge type.

The substituents on the complex of the invention, i.e. the "R" groups other than hydrogen, are those groups which result in complexes having improved stability, controlled lipophilicity, improved hydrogen bonding and greater rigidity of the macrocyclic ligand.

Regarding rigidity of the macrocycle, groups which rigidify the macrocycle typically result in improved stability and improved inner- and outer-sphere relaxation. Examples of groups which improve rigidity of the macrocycle include, but are not limited to, cycloalkyl groups e.g. trans-cyclohexano, and multiple alkyl or substituted alkyl groups.

Regarding hydrogen bonding, groups that improve hydrogen bonding result in improved residence time of water to the metal complex by providing alternate binding sites. Examples of groups that improve hydrogen bonding include, but are not limited to, hydroxy alkyl or amino alkyl, e.g. hydroxymethyl or aminopropyl.

By varying the type and number of substitutents, e.g. "R" groups which are other than hydrogen, the lipophilicity of the complexes can be controlled, i.e. the biodistribution of the complexes of the invention can be controlled, by preparing compounds which vary from hydrophilic to lipophilic. Therefore, the complexes of the invention can be targeted to various tissues or organs in the body by controlling the type and number of substitutents.

Kinetic stability of the metal complex is important because complexes which are not sufficiently kinetically stable dissociate and release free metal in the body. The kinetic stability, $k_{diss}$ ($M^{-1}sec^{-1}$), can be controlled by varying the type and number of substitutents which are other than hydrogen. Oxidative stability of the metal complex is a particular problem for Mn complexes and is important because complexes which are not sufficiently oxidatively stable will go from Mn(II) to Mn(III). Since the Mn(III) complexes are colored, it is necessary to maintain the complexes in the Mn(II) form to have a suitable contrast agent. By varying the type and number of substitutents, the oxidative stability, $E_{1/2}(v)$, is controlled. It is generally desired to select the type and number of substitutents such that $E_{1/2}$ is greater than about 0.7v.

A first embodiment of the invention relates to a method of magnetic resonance imaging comprising (a) administering to a human or non-human animal subject a contrast medium comprising a physiologically compatible complex of the invention and a nontoxic pharmaceutically acceptable carrier, adjuvant or vehicle; and (b) generating a magnetic resonance image of at least a part of the human or non-human animal subject.

A second embodiment of the invention relates to a method of diagnostic imaging comprising (a) administering to a human or non-human animal subject a diagnostic agent comprising a physiologically compatible complex of the present invention and a nontoxic, pharmaceutically acceptable carrier, adjuvant or vehicle, and (b) generating an X-ray, ultrasound or scintigraphic image of at least a part of the human or non-human animal subject.

A third embodiment of the invention relates to a method of radiotherapy practiced on a human or non-human animal subject comprising administering to the human or non-human animal subject a radioactive agent comprising a physiologically compatible complex of the present invention wherein M is a radioactive metal, and a nontoxic, pharmaceutically acceptable carrier, adjuvant or vehicle.

The macrocyclic ligands useful in the complexes of the present invention can be prepared according to the general procedure shown in Scheme A set forth below. Thus, an amino acid amide, which is the corresponding amide derivative of a naturally or non-naturally occurring α-amino acid, is reduced to form the corresponding substituted ethylenediamine. Such amino acid amide can be the amide derivative of any one of many well known amino acids. Preferred amino acid amides are those represented by the formula:

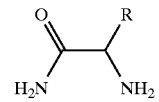

wherein R is derived from the D or L forms of the amino acids Alanine, Aspartic acid, Arginine, Asparagine, cysteine, Glycine, Glutamic acid, Glutamine, Histidine, Isoleucine, Leucine, Lysine, Methionine, Proline, Phenylalanine, Serine, Tryptophan, Threonine, Tyrosine, Valine and/or the R groups of unnatural α-amino acids such as alkyl, ethyl, butyl, tert-butyl, cycloalkyl, phenyl, alkenyl, allyl, alkynyl, aryl, heteroaryl, polycycloalkyl, polycycloaryl, polycycloheteroaryl, imines, aminoalkyl, hydroxyalkyl, hydroxyl, phenol, amine oxides, thioalkyl, carboalkoxyalkyl, carboxylic acids and their derivatives, keto, ether, aldehyde, amine, nitrile, halo, thiol, sulfoxide, sulfone, sulfonic acid, sulfide, disulfide, phosphonic acid, phosphinic acid, phosphine oxides, sulfonamides, amides, amino acids, peptides, proteins, carbohydrates, nucleic acids, fatty acids, lipids, nitro, hydroxylamines, hydroxamic acids, thiocarbonyls, borates, boranes, boraza, silyl, siloxy, silaza, and combinations thereof. Most preferred are those wherein R represents hydrogen, alkyl, cycloalkylalkyl, and aralkyl radicals. The diamine is then tosylated to produce the di-N-tosyl derivative which is reacted with a di-O-tosylated tris-N-tosylated triazaalkane diol to produce the corresponding substituted N-pentatosylpentaazacycloalkane. The tosyl groups are then removed and the resulting compound is reacted with a metal compound, e.g. a manganese(II) compound, under essentially anhydrous and anaerobic conditions to form the corresponding substituted metal, e.g. manganese(II), pentaazacycloalkane complex. When the ligands or charge-neutralizing anions, i.. X, Y and Z, are anions or ligands that cannot be introduced directly from the metal, e.g. manganese, compound, the complex with those anions or ligands can be formed by conducting an exchange reaction with a complex that has been prepared by reacting the macrocycle with a metal, e.g. manganese, compound.

The complexes of the present invention, wherein $R_9$, and $R_2$ are alkyl, and $R_3$, $R'_3$, $R_4$, $R'_4$, $R_5$, $R'_5$, $R_6$, $R'_6$, $R_7$, $R'_7$, $R_8$ and $R'_8$ can be alkyl, arylalkyl or cycloalkylalkyl and R or R' and $R_1$ or $R'_1$ together with the carbon atoms they are attached to are bound to form a nitrogen containing heterocycle, can also be prepared according to the general procedure shown in Scheme B set forth below utilizing methods known in the art for preparing the metal, e.g. manganese(II), pentaazabicyclo[12.3.1]octadecapentaene complex precursor. See, for example, Alexander et al., Inorg. Nucl. Chem. Lett., 6, 445 (1970). Thus a 2,6-diketopyridine is condensed with triethylene tetraamine in the presence of a metal, e.g. manganese(II), compound to produce the metal, e.g. manganese(II), pentaazabicyclo[12.3.1] octadecapentaene complex. The metal, e.g. manganese(II), pentaazabicyclo[12.3.1]octadecapentaene complex is hydrogenated with platinum oxide at a pressure of 10–1000 psi to give the corresponding metal, e.g. manganese(II), pentaazabicyclo[12.3.1]octadecatriene complex.

The macrocyclic ligands useful in the complexes of the present invention can also be prepared by the diacid dichloride route shown in Scheme C set forth below. Thus, a triazaalkane is tosylated in a suitable solvent system to produce the corresponding tris (N-tosyl) derivative. Such a derivative is treated with a suitable base to produce the corresponding disulfonamide anion. The disultonamide anion is dialkylated with a suitable electrophile to produce a derivative of a dicarboxylic acid. This derivative of a dicarboxylic acid is treated to produce the dicarboxylic acid, which is then treated with a suitable reagent to form the diacid dichloride. The desired vicinal diamine is obtained in any of several ways. One way which is useful is the preparation from an aldehyde by reaction with cyanide in the presence of ammonium chloride followed by treatment with acid to produce the alpha ammonium nitrile. The latter compound is reduced in the presence of acid and then treated with a suitable base to produce the vicinal diamine. Condensation of the diacid dichloride with the vicinal diamine in the presence of a suitable base forms the tris(tosyl)diamide macrocycle. The tosyl groups are removed and the amides are reduced and the resulting compound is reacted with a metal, e.g. manganese (II), compound under essentially anhydrous and anaerobic conditions to form the corresponding substituted pentaazacycloalkane metal, e.g. manganese (II), complex.

The vicinal diamines have been prepared by the route shown (known as the Strecker synthesis) and vicinal diamines were purchased when commercially available. Any method of vicinal diamine preparation could be used.

The macrocyclic ligands useful in the complexes of the present invention can also be prepared by the pyridine diamide route shown in Scheme D as set forth below. Thus, a polyamine, such as a tetraaza compound, containing two primary amines is condensed with dimethyl 2,6-pyridine dicarboxylate by heating in an appropriate solvent, e.g., methanol, to produce a macrocycle incorporating the pyridine ring as the 2,6-dicarboxamide. The pyridine ring in the macrocycle is reduced to the corresponding piperidine ring in the macrocycle, and then the diamides are reduced and the resulting compound is reacted with a metal, e.g. manganese (II), compound under essentially anhydrous and anaerobic conditions to form the corresponding substituted pentaazacycloalkane metal, e.g. manganese (II), complex.

The macrocyclic ligands useful in the complexes of the present invention can also be prepared by the bis (haloacetamide) route shown in Scheme E set forth below. Thus a triazaalkane is tosylated in a suitable solvent system to produce the corresponding tris (N-tosyl) derivative. Such a derivative is treated with a suitable base to produce the corresponding disulfonamide anion. A bis(haloacetamide), e.g., a bis(chloroacetamide), of a vicinal diamine is prepared by reaction of the diamine with an excess of haloacetyl halide, e.g., chloroacetyl chloride, in the presence of a base. The disulfonamide anion of the tris(N-tosyl) triazaalkane is then reacted with the bis(chloroacetamide) of the diamine to produce the substituted tris(N-tosyl)diamide macrocycle. The tosyl groups are removed and the amides are reduced and the resulting compound is reacted with a metal, e.g. manganese (II), compound under essentially anhydrous and anaerobic conditions to form the corresponding substituted pentaazacycloalkane metal, e.g. manganese (II), complex.

The macrocyclic ligands useful in the complexes of the present invention, wherein $R_1$, $R'_1$, $R_2$, $R'_2$ are derived from a diamino starting material and $R_5$, $R'_5$, $R_7$, $R'_7$ and $R_9$, $R'_9$ can be H or any functionality previously described, can be prepared according to the pseudo-peptide method shown in Scheme F set forth below. A substituted 1,2-diaminoethane represented by the formula,

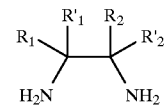

wherein $R_1$, $R'_1$, $R_2$ and $R'_2$ are the substituents on adjacent carbon atoms in the product macrocyclic ligand as set forth above, can be used in this method in combination with any amino acids. The diamine can be produced by any conventional method known to those skilled in the art. The R groups in the macrocycle derived from substituents on the α-carbon of α-amino acids, i.e. $R_5$, $R'_5$, $R_7$, $R'_7$, $R_9$ and R 9, could be derived from the D or L forms of the amino acids Alanine, Aspartic acid, Arginine, Asparagine, Cysteine, Glycine, Glutamic acid, Glutamine, Histidine, Isoleucine, Leucine, Lysine, Methionine, Proline, Phenylalanine, Serine, Tryptophan, Threonine, Tyrosine, Valine and/or the R groups of unnatural α-amino acids such as alkyl, ethyl, butyl, tert-butyl, cycloalkyl, phenyl, alkenyl, allyl, alkynyl, aryl, heteroaryl, polycycloalkyl, polycycloaryl, polycycloheteroaryl, imines, aminoalkyl, hydroxyalkyl, hydroxyl, phenol, amine oxides, thioalkyl, carboalkoxyalkyl, carboxylic acids and their derivatives, keto, ether, aldehyde, amine, nitrile, halo, thiol, sulfoxide, sulfone, sulfonic acid, sulfide, disulfide, phosphonic acid, phosphinic acid, phosphine oxides, sulfonamides, amides, amino acids, peptides, proteins, carbohydrates, nucleic acids, fatty acids, lipids, nitro, hydroxylamines, hydroxamic acids, thiocarbonyls, borates, boranes, boraza, silyl, siloxy, silaza, and combinations thereof. As an example 1,8-dihydroxy, 4,5-diaminooctane is monotosylated and reacted with Boc anhydride to afford the differentiated N-Boc, N-tosyl derivative. The sulfonamide was alkylated with methyl bromoacetate using sodium hydride as the base and saponified to the free acid. The diamine containing N-tosylglycine serves as a dipeptide surrogate in standard solution-phase peptide synthesis. Thus, coupling with a functionalized amino acid ester affords the corresponding pseudo-tripeptide. Two sequential TFA cleavage-couplings affords the pseudo-pentapeptide which can be N- and C-terminus deprotected in one step using HCl/AcOH. DPPA mediated cyclization followed by LiAlH$_4$ or Borane reduction affords the corresponding macrocylic ligand. This ligand system is reacted with a metal, e.g. manganese (II), compound, such as manganese (II) chloride under essentially anaerobic conditions to form the corresponding functionalized manganese (II) pentaazacycloalkane complex. When the ligands or charge-neutralizing anions, i.e. X, Y and Z, are anions or ligands that cannot be introduced directly from the metal, e.g. manganese, compound, the complex with those anions or ligands can be formed by conducting an exchange reaction with a complex that has been prepared by reacting the macrocycle with a metal, e.g. manganese, compound.
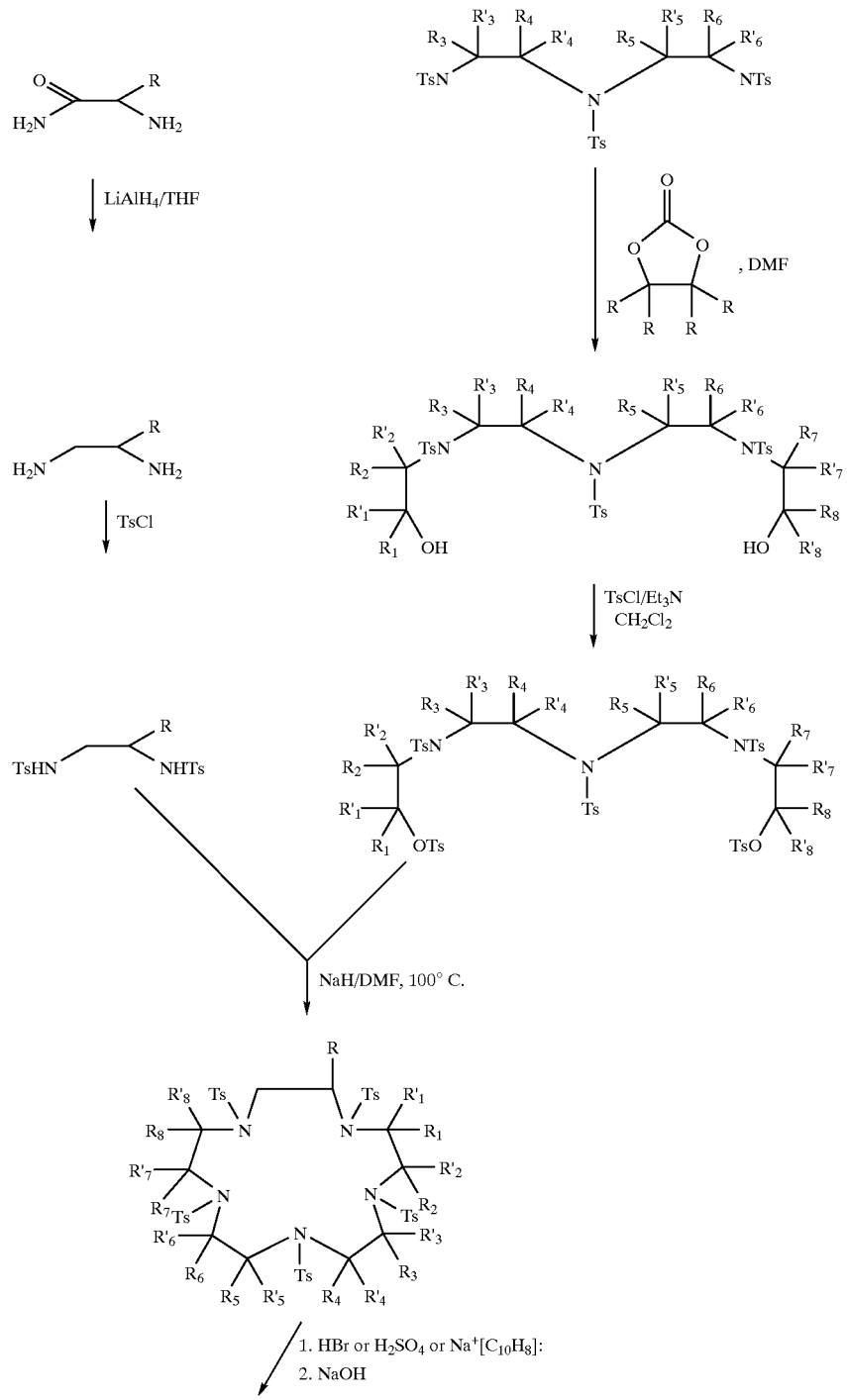

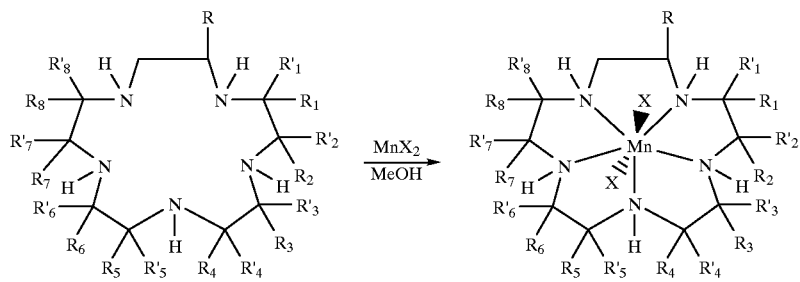
SCHEME B
SCHEME C

-continued
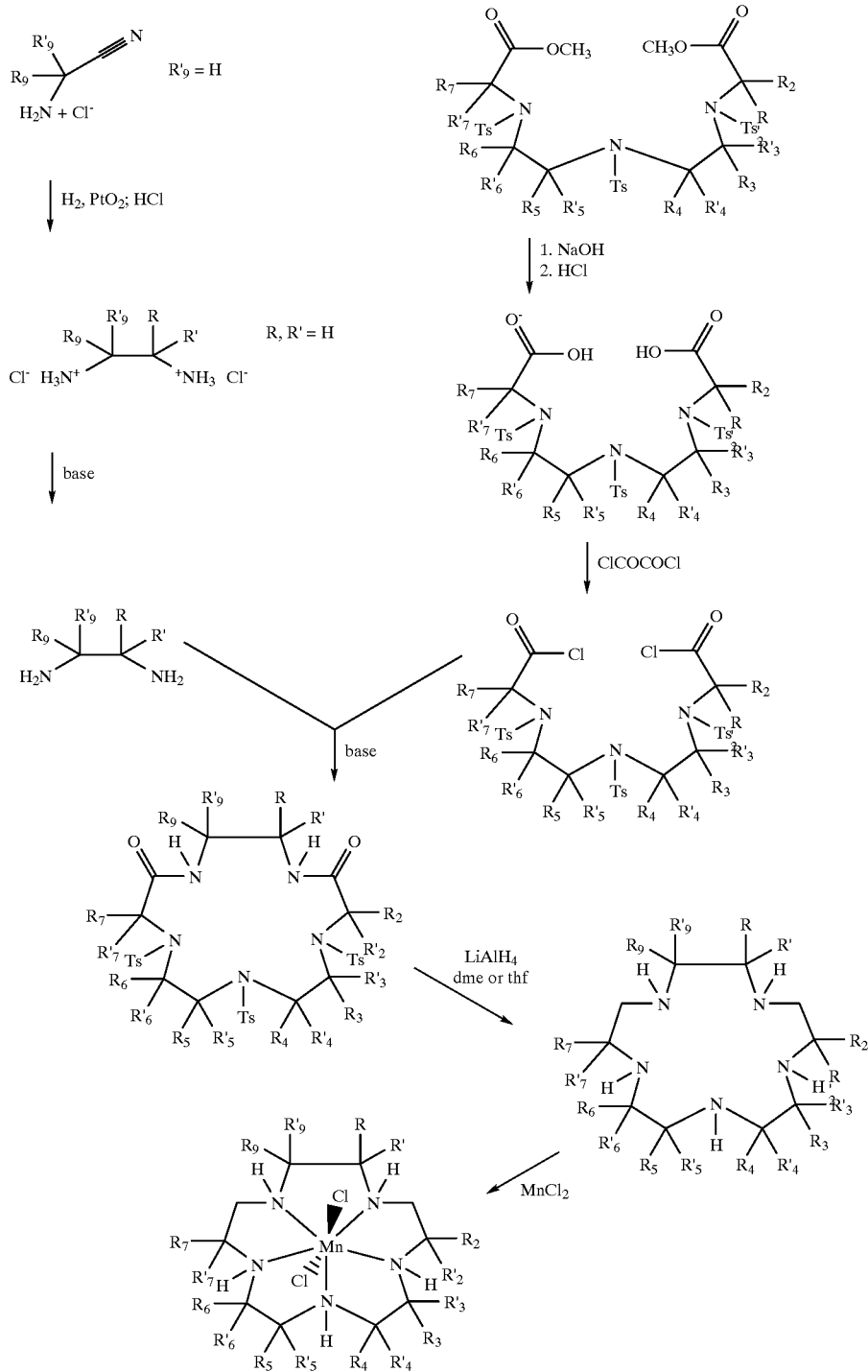

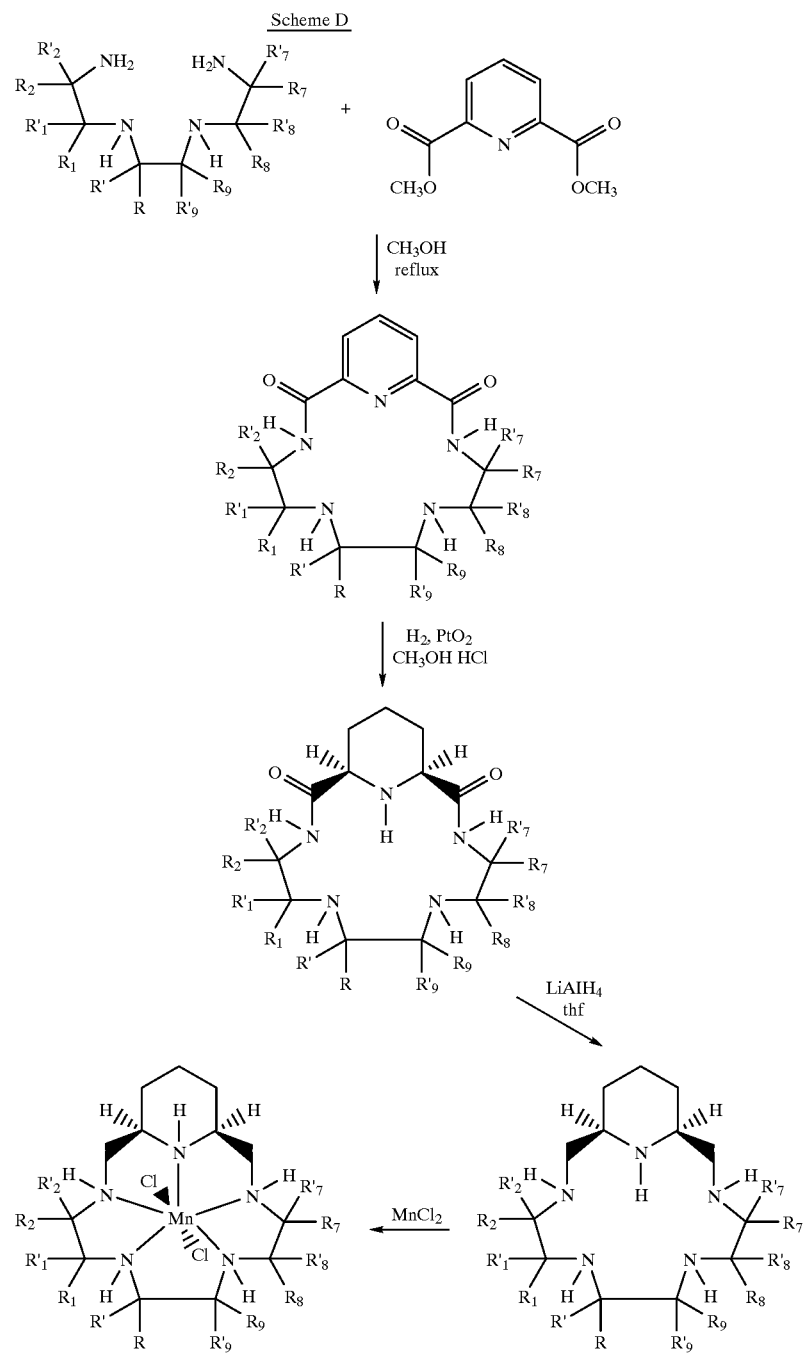

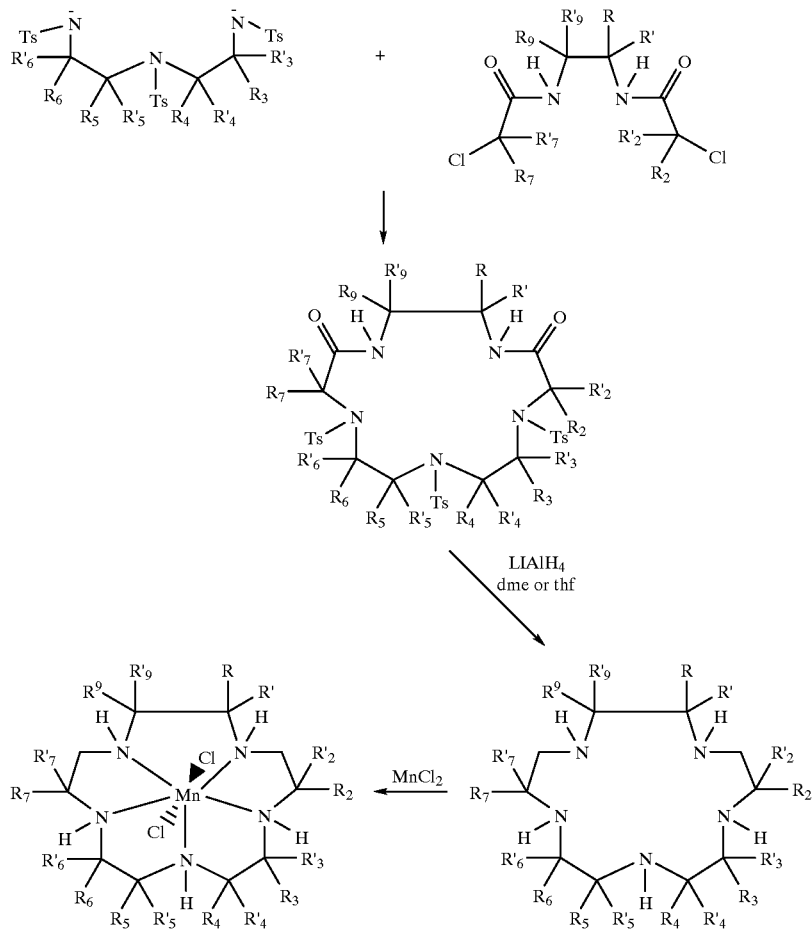
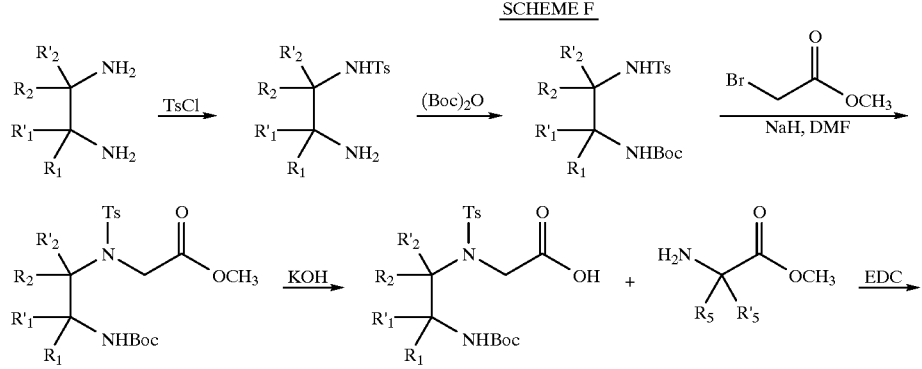

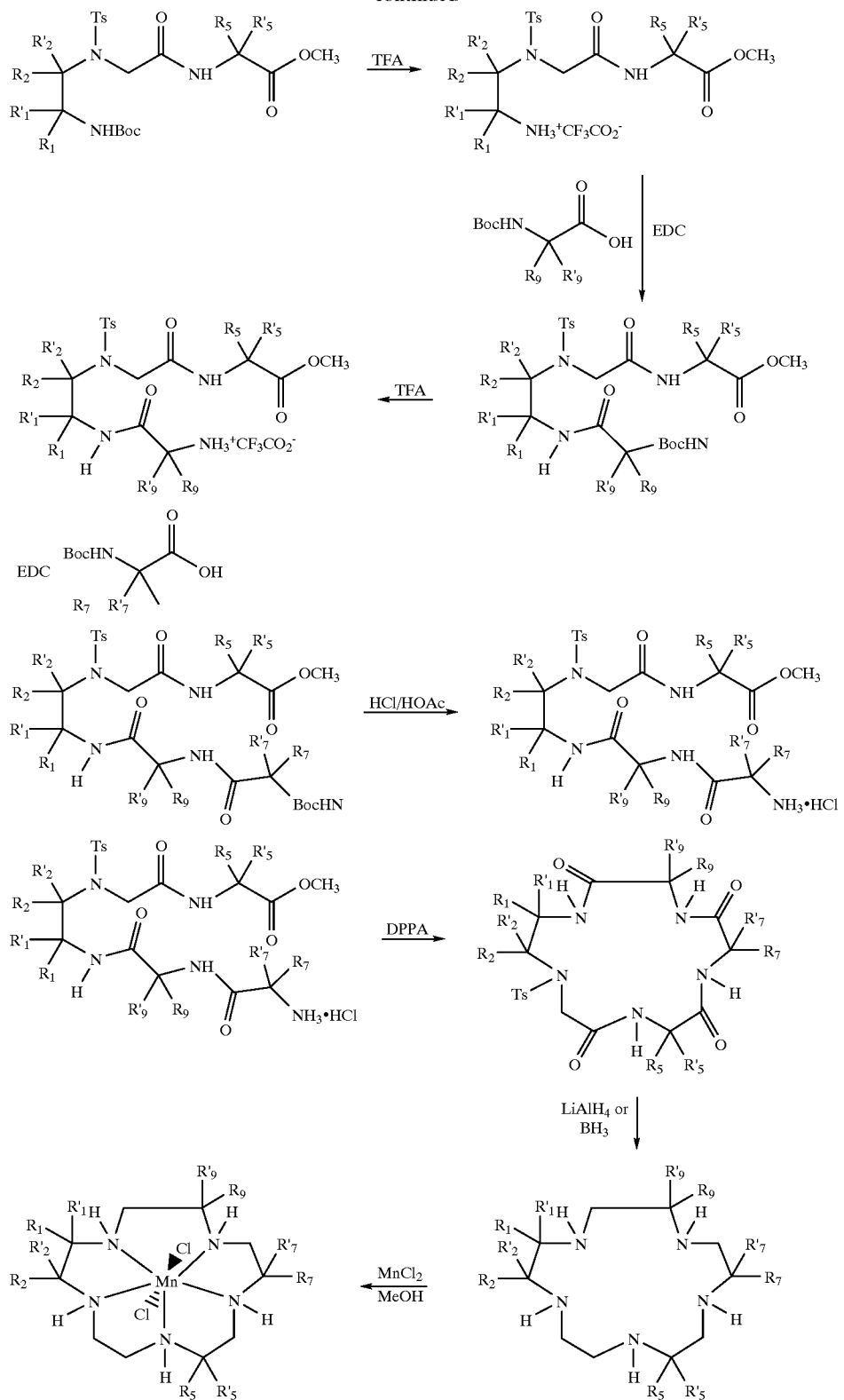

The pentaazamacrocycles of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

The methods of diagnostic analysis of the present invention involve administering the complexes, i.e. contrast enhancing agents, of the invention to a human or non-human animal subject or host, in an amount sufficient to effect the desired contrast (or shift) and then subjecting the host to diagnostic analysis. Preferably diagnostic analysis is NMR analysis; including and especially preferred, NMR imaging analysis (or MRI). Further, the complexes of the present invention are useful in diagnostic analysis by X-ray image analysis, ultrasonic analysis or scintigraphic analysis. While described primarily as contrast enhancing agents, the complexes of the invention can act as NMR shift reagents and such use is contemplated by the methods herein.

The complexes of the invention used as contrast enhancing agents are administered in an amount sufficient to effect the desired contrast. For NMR, this amount is an NMR signal effecting amount of the complex, i.e. any amount of said complex that will alter the spin-lattice, spin-spin or spin-echo relaxation times of an NMR signal or for a shift reagent, selectively shift the spectrical position of a resonance nucleus relative to other similar nuclei. This alteration is effected in a manner in order to enhance the signals received from the subject under analysis either by reducing the aforementioned relaxation times or by increasing them with respect to an area of the host or the host per se which has had the complex administered to it. In another embodiment, the NMR signal effecting amount of the complex is that amount which in addition to changing the relaxation times of the NMR signals in the host, will also change such relaxation times sufficiently so that sharper lines of definition or higher contrast is obtained between those parts of the host that have and have not been administered the complex.

The relaxation time $T_1$ (called the spin-lattice) measures the rate at which magnetic energy is transferred from the resonance nuclei to all other energetic degrees of freedom excluding other resonance nuclei. The relaxation time $T_2$ (spin-spin) measures the rate of magnetization transfer to other resonance nuclei.

Another parameter which can be measured is the density P of the protons in the medium. As a first approximation, it represents the quantity of free water contained in the sample.

The image by nuclear magnetic resonance represented the distribution of these parameters $\rho$, $T_1$, $T_2$ or their combination. The contrast between a given tissue and the adjacent tissues increases as a function of the tissues containing more or less water or mobile protons and differing relaxation times. It is also possible to modify the contrast by varying one or more of these parameters (experimentally echoes of spins aiding the function of $T_2$, or reversal-recovery of the magnetization permitting the local measurement of $T_1$). Experience has shown that it was of greater interest to modify the relaxation time to improve the contrast of the image which can be accomplished, for example, with the contrast enhancing agents provided herein. The density of the protons (in practice those of water and lipids) varies little between individual organs and often less between normal and pathological tissues. However, the relaxation characteristics are dependent on a larger number of factors (microscopic dynamics of the molecules, chemical exchange, paramagnetic disturbances, etc.) which are much more variable.

A detailed discussion of NMR and theoretical considerations in selecting the appropriate parameters for diagnostic analysis, e.g. MRI, is rendered in U.S. Pat. No. 4,749,560 which is incorporated herein by reference. X-ray image analysis, ultrasonic diagnosis, scintigraphic image analysis and radiotherapy utilizing the complexes of the invention are all conducted in accordance with well-established techniques known to those of ordinary skill in the art.

Moreover, the method of-diagnostic analysis of the invention allows tissue or organ-specific diagnostic analysis to be achieved. For example, the contrast enhancing agents can exhibit organ and tissue specificity, e.g. biodifferental distribution, such as in myocardial tissue when the complexes of the invention are lipophilic in nature.

The complexes of the invention may be administered to a host as a pharmaceutical composition in a contrast-enhancing amount. The pharmaceutical compositions contain a contrast-enhancing dosage of the contrast agents according to the invention together with a nontoxic pharmaceutically acceptable carrier, adjuvant or vehicle. The compositions can be administered by well-known routes including oral, intravenous (if soluble), intramuscular, intranasal, intradermal, subcutaneous, parenteral, enteral and the like. Depending on the route of administration, the pharmaceutical composition may require protective coatings.

The pharmaceutical forms suitable for injectable use includes sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water, buffered aqueous solutions (i.e. biocompatable buffers), ethanol, polycl (glycerol, propylene glycol, polyethylene glycol, and the like), suitable mixtures thereof, surfactants or vegetable oils. Sterilization can be accomplished by any art recognized technique, including but not limited to, addition of antibacterial or antifungal agents, for example, paraben, chlorobutanol, phenol, sorbic acid, thimerosal, and the like. Further, isotonic agents, such as sugars or sodium chloride may be incorporated in the subject compositions.

Production of sterile injectable solutions containing the subject contrast agent is accomplished by incorporating these agents in the required amount in the appropriate solvent with various ingredients enumerated above, as required, followed by sterilization, preferably filter sterilization. To obtain a sterile powder, the above solutions are vacuum-dried or freeze-dried as necessary.

Solid dosage forms for oral administration may include capsules, tablets, pills, powders, granules and gels. In such solid dosage forms, the active compound may be admixed with at least one inert diluent such as sucrose, lactose or starch. Such dosage forms may also comprise, as in normal practice, additional substances other than inert diluent, e.g. lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluent commonly used in the art, such as water. Such compositions may also comprise adjuvants, such as wetting agents, emulsifying and suspending agents, and sweetening, flavoring, and perfuming agents.

The contrast agents of the inventions are thus compounded for convenient and effective administration in pharmaceutically effective amounts with a suitable pharmaceutically acceptable carrier, adjuvant or vehicle in a dosage which effects contrast enhancement. These amounts are preferably about 1 μmol to 1 mol of the contrast agent per liter and/or administered in doses of about 0.001 to 5 mmol/kg body weight. Preferred compositions provide effective-dosages of contrast agents in the range of about 0.001–5 mmol/kg for NMR diagnostics, preferably about 0.005–0.5 mmol/kg; in the range of about 0.1–5 mmol/kg for X-ray diagnostics; and in the range of about 0.1–5 mmol/kg for ultrasound diagnostics. For scintigraphic diagnostics, the dose of the contrast agent should generally be lower than for NMR diagnostics, e.g. MRI. For radiotherapy, conventional doses known to those of ordinary skill in the art can be used.

As used herein, a pharmaceutically acceptable carrier, adjuvant or vehicle includes any and all solvents, dispersion media, coatings, antibacterial and antifungal agents, isotonic agents, and the like. The use of such media and agents are well known in the art.

Contemplated equivalents of the general formulas set forth above for the compounds and derivatives as well as the intermediates are compounds otherwise corresponding thereto and having the same general properties such as tautomers of the compounds and such as wherein one or more of the various R groups are simple variations of the substituents as defined therein, e.g., wherein R is a higher alkyl group than that indicated, or where the tosyl groups are other nitrogen or oxygen protecting groups or wherein the O-tosyl is a halide. Anions having a charge other than 1, e.g., carbonate, phosphate, and hydrogen phosphate, can b, used instead of anions having a charge of 1, so long as they do not adversely affect the overall activity of the complex. However, using anions having a charge other than 1 will result in a slight modification of the general formula for the complex set forth above. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

All reagents were used as received without purification unless otherwise indicated. All NMR spectra were obtained on a Varian VXR-300 or VXR-400 nuclear magnetic resonance spectrometer. Qualitative and quantitative mass spectroseopy was run on a Finnigan MAT90, a Finnigan 4500 and a VG40-250T using m-nitrobenzyl alcohol(NBA), m-nitrobenzyl alcohol/LiCl (NBA - Li) or m-nitrobenzyl alcohol (NBA - HC). Melting points (mp) are uncorrected.

The following abbreviations are in accordance with common usage.

| DMSO | Dimethylsulfoxide |
|------|-------------------|
| THF | Tetrahydrofuran |
| DMF | Dimethylformamide |

Example 1

Synthesis of [Manganese(II) dichloro-(trans-2,3-bis (3-hydroxypropyl)-1.4.7.10.13- pentaazacyclopentadecane)]

1.A. Synthesis of D.L-4.5-Diamino-1,7-octadiene

D,L-4,5-Diamino-1,7-octadiene was prepared according to (1) with the following modifications: D,L-4,5-bis (diphenylmethylamino)-1,7-octadiene (76.2 g, 161 mmol) was dissolved in trifluoroacetic acid (150 ml) under a dry argon atmosphere and triethylsilane (75.0 g, 645 mmol) was then added. The red-brown solution was refluxed for 30 minutes and the solvent was removed in vacuo. The residue was dissolved in IN HCl (500 ml) and concentrated to a volume of 200 ml in vacuo. Then, IN HCl (800 ml) was added and the solution was washed with $CH_2Cl_2$ (3×500 ml) and ethyl ether (500 ml). The solvent was removed in vacuo and the crude product was crystallized from methanol-ethyl ether to give 28.1 g (81.9% yield) of the hydrochloride salt as colorless needles: mp 190–3° C.; $^1H$ NMR (DMSO-$d_6$, 400 MHz) δ2.37 (m, 2H), 2.63 (m, 2H), 3.58 (m, 2H), 5.20 (d, J=10.2 Hz, 2H), 5.28 (dd, J=1.47, 18.6 Hz, 2H), 5.79 (m, 2H), 8.65 (br s, 6H); $^{13}C$ NMR (DMSO-$d_6$, 100 MHz) δ 31.59, 51.01, 119.71, 132.33; PAB mass spectrum (GT-HCl) m/z 141 [M+H]$^+$.

D,L-4,5-Diamino-1,7-octadiene dihydrochloride (28.0 g, 131 mmol) was slurried in MeOH (50 ml) and a solution of KOH (14.7 g, 262 mmol) in MeOH (30 ml) was added dropwise under an argon atmosphere with stirring. Ethyl ether (1 1) was added and the mixture was then dried with $Na_2SO_4$. The salts were filtered and washed with ethyl ether. The filtrate was concentrated in vacuo to give 17.7 g (95.9% yield) of the diamine as a light yellow liquid: $^1H$ NMR (CDCl$_3$, 300 MHz) δ 1.34 (s, 4H), 2.07 (m, 2H), 2.31 (m, 2H), 2.69 (m, 2H), 5.12 (m, 4H), 5.81 (m, 2H); $^{13}C$ NMR (CDCl$_3$, 75 MHz) δ 39.68, 54.43, 117.29, 135.98.

References (1) Neumann, W. L., Rogic, M. M. and Dunn, J. T., Tetrahedron Lett., 32, 5865–8 (1991).

1.B. Synthesis of D,L-N,N'-Bis(chloroacetyl)-4.5-diamino-1, 7-octadiene

To a stirred solution of D,L-4,5-diamino-1,7-octadiene prepared as in Example 1A (17.5 g, 124 mmol) in alcohol-free $CHCl_3$ (590 ml) was added $H_2O$ (120 ml) and the resulting mixture was cooled to 0° C. Solutions of chloroacetyl chloride (43.1 g, 382 mmol) in alcohol-free $CHCl_3$ (235 ml) and $K_2CO_3$ (49.3 g, 357 mmol) in $H_2O$ (495 ml) were added simultaneously under an argon atmosphere over 1.75 h while maintaining the temperature at 0° C. The mixture was then allowed to warm to room temperature while stirring an additional 2 h. The layers were separated and the aqueous layer was extracted with $CHCl_3$ (1 l). The combined $CHCl_3$ layers were washed with $H_2O$ (3×500 ml), saturated NaCl solution and were dried ($MgSO_4$). The solvent was removed in vacuo to give 35.9 g (98.4% yield) of the product as a white crystalline solid: mp 120–2° C.; $^1H$ NMR ($CDCl_3$, 400 MHz) δ 2.37 (m, 2H), 2.44 (m, 2H), 4.03 (m, 6H), 5.16 (m, 4H), 5.76 (m, 2H), 6.90 (d, J=5.4 Hz, 2H); $^{13}C$ NMR ($CDCl_3$, 100 MHz) 6 36.08, 42.59, 52.33, 119.07, 132.83, 166.68; CI mass spectrum ($CH_4$) m/z 293 $[M+H]^+$.

1.C. Synthesis of D,L-5,6-Bis(2-propenyl)-1,10,13-tris-(D-toluenesulfonyl)-1.4.7.10.13-pentaazacyclopentadecane-3.8-dione A solution of 1,4,7-tris(p-toluenesulfonyl)-1,4,7-triazaheptane-1,7-disodium salt (61.0 g, 100 mmol), prepared according to the procedure described in Example 1 of EP Patent Application 0 524 161 A1, in degassed anhydrous DMF (1 l) and a solution of D,L-N,N -bis(chloroacetyl)-4,5-diamino-1,7-octadiene (29.3 g, 100 mmol) in degassed anhydrous DMF (1 l) were simultaneously added to degassed anhydrous DMF (4 l) under a dry argon atmosphere at room temperature over 4.5 h. The mixture was then stirred for an additional 18 h at room temperature and the solvent was removed in vacuo. The residue was dissolved in $CH_2Cl_2$ (1 l), washed with $H_2O$ (2×1 l), saturated NaCl solution (500 ml) and was dried ($MgSO_4$). The solvent was removed in vacuo to give the crude product as a yellow crystalline solid. The solid was dissolved in $CH_2Cl_2$ and MeOH (2 l) was added. Crystallization by removal of the $CH_2Cl_2$ in vacuo gave 47.7 g (60.7% yield) of the product as colorless needles: mp 180–2° C.; $^1H$ NMR ($CDCl_3$, 300 MHz) δ 1.60 (br s, 2H), 2.26 (m, 2H), 2.45 (s, 9H), 3.19 (m, 4H), 3.45 (m, 4H), 3.70 (dd, J=11.6, 16.1 Hz, 4H), 4.01 (m, 2H), 5.16 (s, 2H), 5.21 (d, J=6.1 Hz, 2H), 5.75 (m, 2H), 6.55 (d, J=7.3 Hz, 2H), 7.33 (m, 6H), 7.70 (m, 6H); $^{13}C$ NMR ($CDCl_3$, 100 MHz) δ 21.58, 36.00, 49.63, 51.50, 51.71, 54.33, 119.63, 127.51, 127.69, 129.95, 130.09, 132.14, 133.99, 134.40, 143.92, 144.44, 168.37; FAB mass spectrum (NBA-Li) 792.2 $[M+Li]^+$.

1.D Synthesis of D,L-5.6-Bis(3-hydroxypropyl)-1,10,13-tris-(p-toluenesulfonyl)-1,4,7,10,13-pentaazacyclopentadecane-3.8-dione To a stirred suspension of D,L-5,6-bis(2-propenyl)-1,10,13-tris-(p-toluenesulfonyl)-1,4,7,10,13-pentaazacyclopentadecane-3,8-dione (20.0 g, 25.5 mmole), prepared as in Example 1C, in anhydrous THF (300 ml) under a dry argon atmosphere was added a solution of borane in THF (63.6 ml–1.0 M, 63.6 mmole) dropwise over 30 min at 0° C. The solid had dissolved by the end of the addition and stirring was continued at 0° C. for another 3 h. Water (10 ml) was then added to destroy excess borohydride and 3 M NaOH (21.2 ml) was then added also at 0° C. Then 30% $H_2O_2$ (7.23 ml) was added at 0° C. and the resulting colorless solution was allowed to warm to room temperature while stirring for another 30 min. Saturated NaCl solution (200 ml) was added to the solution and the product was extracted with ethyl ether (2×500 ml). The organic layers were combined and washed with saturated NaCl solution (2×100 ml). Product had begun to crystallize from the ether solution. The solvent was removed in vacuo to give a crystalline solid. Crystallization from MeOH—ethyl ether gave 18.2 g (87.0 t) of the product containing secondary alcohol by product. Recrystallization of this from $CHCl_3$—ethyl ether gave 13.8 g (65.9%) of the product as colorless needles: mp 220–2° C.; $^1H$ NMR ($CDCl_3$, 300 MHz) δ 1.62 (m, 6H), 1.80 (m, 2H), 2.42 (s, 6H), 2.43 (s, 3H), 2.63 (br s, 2H), 3.17 (m, 2H), 3.21 (m, 2H), 3.45 (m, 4H), 3.60 (m, 6H), 3.91 (d, J =17.1 Hz, 2H), 3.97 (m, 2H), 7.15 (d, J =8.3 Hz, 2H), 7.32 (d, J =8.3 Hz, 6H), 7.65 (d, J =8.3 Hz, 2H), 7.71 (d, J=8.3 Hz, 4H); $^{13}C$ NMR ($CDCl_3$, 100 MHz) δ 21.58, 27.96, 28.80, 49.51, 51.56, 52.68, 54.18, 62.09, 127.45, 127.66, 129.94, 130.09, 133.96, 134.44, 143.86, 144.46, 168.73; FAB mass spectrum (NBA-Li) m/z 828 $[+H]^+$.

1.E. Synthesis of D.L-2,3-Bis(3-hydroxypropyl)-1,4,7,10,13-pentaazacyclopentadecane To a stirred suspension of D,L-5,6-bis(3-hydroxypropyl)-1,10,13-tris(p-toluenesulfonyl)-1,4,7,10,13-pentaazacyclopentadecane-3,8-dione (5.00 g, 6.08 mmole), prepared as in Example 1D, in anhydrous THF (100 ml) under a dry argon atmosphere was added a solution of 1.0 M $LiAlH_4$ in THF (76.0 ml, 76.0 mmole) dropwise over 5 minutes The yellow homogeneous solution was refluxed for 30 h (by which time it had become heterogeneous) and was then cooled to 0° C. The mixture was then quenched by the dropwise addition of saturated $Na_2SO_4$ (15 ml) while cooling in an ice bath. The solvent was removed in vacuo and any remaining water was removed by azeotroping with toluene (3×500 ml) and then hexanes (3×500 ml). The solids were then extracted with refluxing, anhydrous, inhibitor-free THF (2×500 ml and 2×700 ml), filtering the solid each time under an argon atmosphere. The solvent was removed in vacuo from the extracts to give oils which rapidly crystallized. The crude product was purified by crystallization from acetonitrile—ethyl ether to give 500 mg (24.8%) of a colorless crystalline solid: mp 105–6° C.; $^1H$ NMR ($CDCl_3$, 400 MHz) δ 1.59 (m, 4H), 1.70 (m, 4H), 2.73 (m, 25H), 3.51 (m, 2H), 3.66 (m, 2H); $^{13}C$ NMR ($CDCl_3$, 100 MHz) 6 26.85, 27.32, 46.89, 47.97, 48.28, 48.70, 58.17, 62.95; CI mass spectrum ($CH_4$) 332 $[M+H]^+$.

1.F. Synthesis of [Manganese (II) dichloro trans-2,3-bis(3-hydroxypropyl)-1,4,7,10,13-pentaazacyclopentadecane)]

To a stirred solution of anhydrous $MnCl_2$ (126 mg, 1.00 mmole) in methanol was added D,L-2,3-bis(3-hydroxypropyl)-1,4,7,10,13-pentaazacyclopentadecane prepared as in Example 1E (331 mg, 1.00 mmole) and the solution was refluxed for 2 h and then stirred at room temperature overnight. The solvent was removed in vacuo and the white solid was redissolved in a mixture of THF (20 ml) and ethanol (3 ml) and filtered through Celite™ diatomaceous earth. The filtrate was concentrated to a volume of 3 ml, ethanol (3 ml) was added and the solution was heated to reflux. THF (20 ml) was added to the solution and the crystals which formed were collected to give 820 mg (69%) of the product as a white solid: FAB mass spectrum (NBA - HCl) m/z (relative intensity) 421/423 $[(M - Cl)^+, 100/33]$; Anal. Calcd. For $C_{16}H_{37}N_5MnCl_2$: C, 42.02; H, 8.15; N, 15.31; Cl, 15.50. Found: C, 42.11; H, 8.14; N, 15.29; Cl, 15.59.

Example 2

Relaxivity measurements of the complex of Example 1 was determined.

Proton relaxation times ($T_1$) of the sample in 100 mM Hepes buffer, pH=7.4, at 40° C. were determined from a monoexponential curve fit obtained from inversion-recovery pulse sequences (180°-τ90°) with a Bruker PC 120/125/10 VTs NMR process analyzer. The spectrometer was calibrated for each sample to assure accurate duration of 90° and 180° radio frequency pulses and appropriate magnetic field strength to match the 20 MHz system operating frequency. The relaxivity ($R_1$) was obtained from the slope of a plot of $1/T_1$ versus the concentration of paramagnetic compound.

The relaxation time ($T_2$)-of each sample in 100 mM Hepes buffer, pH=7.4, was measured at 40° C. using a Carr-Purcel-Meiboom-Gill pulse sequence on the same Bruker instrument. The relaxivity ($R_2$) was obtained from a plot of $1/T_2$ versus the concentration of the paramagnetic compound.

The relaxivity of the complex of Example 1 is as follows: $R_1$ (mM$^{-1}$sec$^{-1}$)=2.46 and $R_2$ (mM$^{-1}$sec$^{-1}$)=3.19.

That which is claimed is:

1. A method of magnetic resonance imaging comprising the steps of administering to a human or non-human animal subject a contrast medium comprising a physiologically compatible complex of the formula:

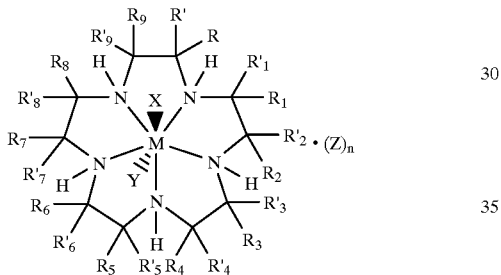

(a) at least one pair of "R" groups on adjacent carbon atoms of the macrocycle selected from the group consisting of $R_9$ or $R'_9$ and R or R', $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$ are independently selected such that (i) at least one "R" group of the pair is a substituted alkyl, substituted alkenyl, substituted alkynyl, substituted cycloalkyl or substituted cycloalkenyl radical wherein the substituents are independently selected from the group consisting of —OR$_{10}$, —NR$_{10}$R$_{11}$, —COR$_{10}$, —CO$_2$R$_{10}$, —CONR$_{10}$R$_{11}$, —O—(—(CH$_2$)$_a$—O)$_b$—R$_{10}$, —SR$_{10}$, —SOR$_{10}$, —SO$_2$R$_{10}$, —SO$_2$NR$_{10}$R$_{11}$, —N(OR$_{10}$)(R$_{11}$), —P(O)(OR$_{10}$)(OR$_{10}$), —R(O)(OR$_{10}$)(R$_{11}$) and —OP(O)(OR$_{10}$)(OR$_{11}$) wherein R$_{10}$ and R$_{11}$ are independently selected from the group consisting of hydrogen and alkyl and a and b are integers independently selected from 1 to 6; and (ii) at most one "R" group of the pair is an alkyl, alkenyl, alkynyl, cycloalkyl or cycloalkenyl radical;

(b) the other "R" groups on the macrocycle are (i) independently selected from the group consisting of hydrogen, alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or (ii) $R_1$ or $R'_1$ and $R_2$ or $R'_2$, $R_3$ or $R'_3$ and $R_4$ or $R'_4$, $R_5$ or $R'_5$, and $R_6$ or $R'_6$, $R_7$ or $R'_7$ and $R_8$ or $R'_8$, $R_9$ or $R'_9$ and R or R' together with the carbon atoms to which they are attached independently form a saturated, partially saturated or unsaturated cyclic having 3 to 20 carbon atoms; or (iii) R or R' and $R_1$ or $R'_1$, $R_2$ or $R'_2$, and $R_3$ or $R'_3$, $R_4$ or $R'_4$ and $R_5$ or $R'_5$, $R_6$ or $R'_6$ and $R_7$ or $R'_7$, and $R_8$ or $R'_8$, and $R_9$ or $R'_9$ together with the carbon atoms to which they are attached form a nitrogen containing-heterocycle having 2 to 20 carbon atoms, provided that when the heterocycle so formed is an aromatic heterocycle which does not contain a hydrogen attached to the nitrogen, the hydrogen attached to the nitrogen in the macrocycle and the R groups attached to the carbon atoms of the macrocycle adjacent to nitrogen are absent;

(d) X, Y and Z are (i) ligands independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, or (ii) independently attached to one or more of the "R" groups;

(e) n is an integer from 0 to 3; and (f) M is a paramagnetic metal selected from the group consisting of metals having atomic numbers 21–29, 42–44 and 57–71;

and a nontoxic, pharmaceutically acceptable carrier, adjuvant or vehicle, and generating a magnetic resonance image of at least a part of said subject.

2. Method of claim 1 wherein M is Mn(II) or Gd(III).

3. Method of claim 2 wherein M is Mn(II).

4. Method of claim 1 wherein $R_{10}$ and $R_{11}$ are hydrogen.

5. Method of claim 1 wherein said substituents are independently selected from the group selected of —$OR_{10}$ and —$NR_{10}R_{11}$.

6. Method of claim 5 wherein the "R" groups of the at least one pair of "R" groups on adjacent carbon atoms of the macrocycle are substituted alkyl groups.

7. Method of claim 1 wherein the "R" groups of the at least one pair of "R" groups on adjacent carbon atoms of the macrocycle are substituted alkyl groups.

8. Method of claim 7 wherein said substituents on the at least one pair of "R" groups on adjacent carbon atoms of the macrocycle are independently selected from —$OR_{10}$.

9. Method of claim 8 wherein the complex is:

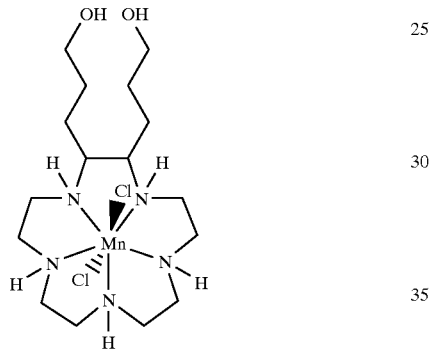

10. Method of claim 1 wherein $R_{10}$ and $R_{11}$ are hydrogen.

11. Method of claim 1 wherein said substituents are independently selected from the group selected of —$OR_{10}$ and —$NR_{10}R_{11}$.

12. Method of claim 11 wherein one "R" group of the at least one pair of "R" groups on adjacent carbon atoms of the macrocycle is an alkyl group and the other "R" group on the adjacent carbon atom of the macrocycle is a substituted alkyl group.

13. Method of claim 1 wherein one "R" group of the at least one pair of "R" groups on adjacent carbon atoms of the macrocycle is an alkyl group and the other "R" group on the adjacent carbon atom of the macrocycle is a substituted alkyl group.

14. Method of claim 13 wherein said substituent on the carbon atom of the at least one pair of "R" groups on adjacent carbon atoms of the macrocycle which is a substituted group is —$OR_{10}$.

15. Method of claim 1 wherein X, Y and Z are independently selected from the group consisting of halide, organic acid, nitrate and bicarbonate anions.

16. A method of imaging comprising the steps of administering to a human or non-human animal subject a contrast medium comprising a physiologically compatible complex of the formula:

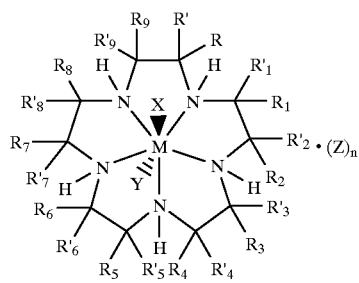

wherein (a) at least one pair of "R" groups on adjacent carbon atoms of the macrocycle selected from the group consisting of $R_9$ or $R'_9$ and R or R', $R_1$, or $R'_1$, and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$ are independently selected such that
  (i) at least one "R" group of the pair is a substituted alkyl, substituted alkenyl, substituted alkynyl, substituted cycloalkyl or substituted cycloalkenyl radical wherein the substituents are independently selected from the group consisting of —$OR_{10}$, —$NR_{10}R_{11}$, —$COR_{10}$, —$CO_2R_{10}$, —$CONR_{10}R_{11}$, —O—(—$(CH_2)_a$—O)$_b$—$R_{10}$, —$SR_{10}$, —$SOR_{10}$, —$SO_2R_{10}$, —$SO_2NR_{10}R_{11}$, —N($OR_{10}$)($R_{11}$), —P(O)($OR_{10}$)($OR_{10}$), —R(O)($OR_{10}$)($R_{11}$) and —OP(O)($OR_{10}$)($OR_{11}$) wherein $R_{10}$ and $R_{11}$ are independently selected from the group consisting of hydrogen and alkyl and a and b are integers independently selected from 1 to 6; and
  (ii) at most one "R" group of the pair is an alkyl, alkenyl, alkynyl, cycloalkyl or cycloalkenyl radical;
(b) the other "R" groups on the macrocycle are
  (i) independently selected from the group consisting of hydrogen, alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or
  (ii) $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, $R_9$ or $R'_9$ and R or R' together with the carbon atoms to which they are attached independently form a saturated, partially saturated or unsaturated cyclic having 3 to 20 carbon atoms; or
  (iii) R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached form a nitrogen containing-heterocycle having 2 to 20 carbon atoms, provided that when the heterocycle so formed is an aromatic heterocycle which does not contain a hydrogen attached to the nitrogen, the hydrogen attached to the nitrogen in the macrocycle and the R groups attached to the carbon atoms of the macrocycle adjacent to nitrogen are absent;
(d) X, Y and Z are
  (i) ligands independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, or (ii) independently attached to one or more of the "R" groups;

(e) n is an integer from 0 to 3; and (f) M is a paramagnetic metal selected from the group consisting of metals having atomic numbers 21–29, 42–44 and 57–71;

and a nontoxic, pharmaceutically acceptable carrier, adjuvant or vehicle, and generating an X-ray, ultrasound or scintigraphic image of at least a part of said subject.

17. Method of claim 16 wherein M is a radioactive metal isotope selected from the group consisting of $^{99m}$Tc and $^{111}$In and said image is a scintigraphic image.

* * * * *